United States Patent [19]
Gysi et al.

[11] Patent Number: 5,571,978
[45] Date of Patent: Nov. 5, 1996

[54] APPARATUS FOR TESTING BOTTLES FOR THE PRESENCE OF CONTAMINATION

[75] Inventors: Peter Gysi, Bellikon; Theo Huesser, Rudolfstetten; Martin Mueller, Unterlunkhofen; Peter M. Robertson, Winkel; Felix Van der Schaar, Seuzach; Melchior Zumbach, Dübendorf, all of Switzerland

[73] Assignee: Elpatronic AG, Zug, Switzerland

[21] Appl. No.: 471,872

[22] Filed: Jun. 7, 1995

Related U.S. Application Data

[62] Division of Ser. No. 88,432, Jul. 7, 1993, Pat. No. 5,520,060.

[30] Foreign Application Priority Data

Jul. 9, 1992 [CH] Switzerland ............... 166/92
Feb. 11, 1993 [CH] Switzerland ............... 415/93
Feb. 11, 1993 [CH] Switzerland ............... 416/93
Mar. 4, 1993 [CH] Switzerland ............... 656/93

[51] Int. Cl.$^6$ ................................... B07C 5/02
[52] U.S. Cl. ........................................ 73/865.8
[58] Field of Search ............... 73/865.8, 864.73, 73/864.81, 863.33, 863.83; 209/522–525; 198/341; 356/240

[56] References Cited

U.S. PATENT DOCUMENTS 5,067,616 11/1991 Plester et al. .

Primary Examiner—Robert Raevis
Attorney, Agent, or Firm—McCormick, Paulding & Huber

[57] ABSTRACT

To detect contamination in used PET returnable bottles, they are fed to a first testing station which takes a gas sample from each bottle. This first testing station tests for the presence of heavy contamination. Heavily contaminated bottles are identified as dirty. The bottles are then fed to a second testing station which takes gas samples from the clean bottles and tests them for contamination with a lower detection threshold. Bottles detected here as contaminated are removed, as are the bottles which fail the first test. The two-stage process allows testing with greater sensitivity while maintaining a high bottle throughput.

4 Claims, 4 Drawing Sheets

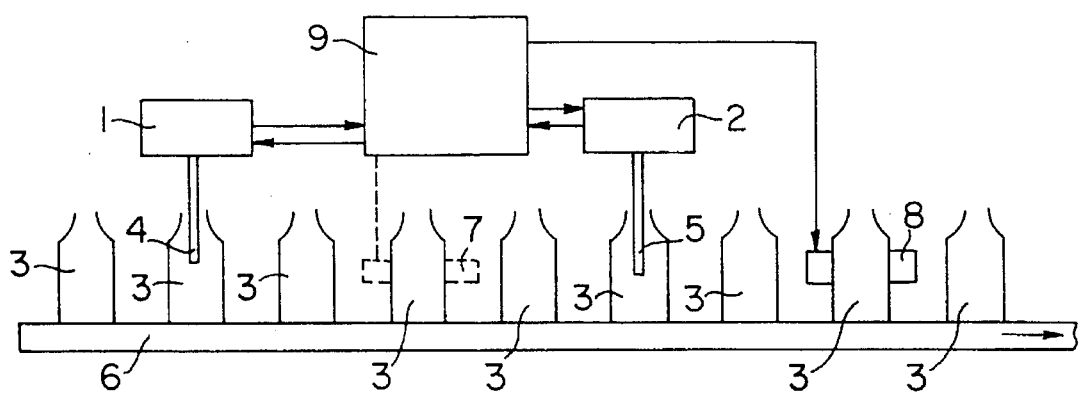
FIG. 1
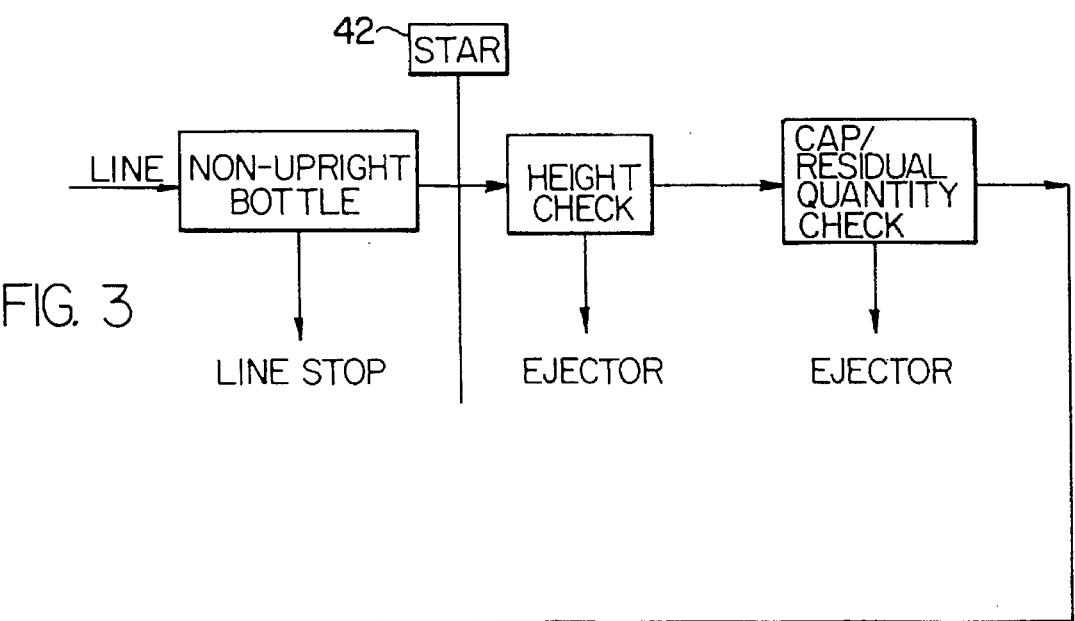
FIG. 3
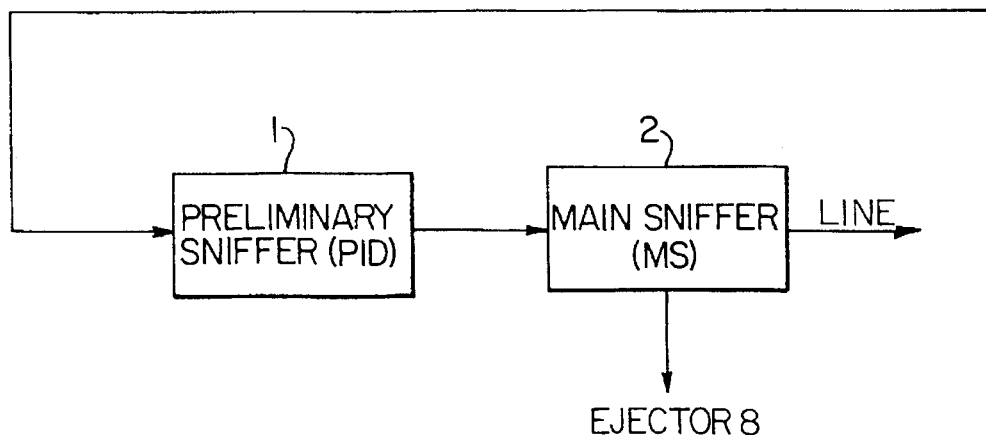

APPARATUS FOR TESTING BOTTLES FOR THE PRESENCE OF CONTAMINATION

CROSS-REFERENCE TO RELATED APPLICATION

This is a divisional of U.S. patent application Ser. No. 08/088,432 filed Jul. 7, 1993, now U.S. Pat. No. 5,520,060 entitled "Process and Apparatus for Testing Bottles For the Presence of Contamination".

BACKGROUND OF THE INVENTION

The invention relates to a process for testing returnable bottles which have been sent back for refilling, in particular PET bottles, for the presence of contamination by testing gas samples taken from individual bottles as the bottles are transported along a conveyor path. The invention also relates to an apparatus for carrying out the process.

For returnable bottles, in particular plastic bottles such as PET bottles, which cannot be washed at high temperatures, the problem arises that contamination needs to be reliably detected in order that contaminated bottles can be removed and not refilled in particular it must be possible to detect returned bottles which a user has used for potentially hazardous substances (poisons, solvents, etc). An already known procedure is to take a gas sample from each bottle and to analyses the sample by photo-ionization detection (PID). This enables undesired substances present even in small traces in the bottle and/or in the plastic material to be detected. As such testing devices need to have a high throughput of bottles per minute (say 250 to 300 bottles per minute) to enable this kind of testing to be undertaken in an industrial bottling plant, a large number of individual PID units have hitherto been used, with each of a number of bottles to be tested having on individual PID unit assigned to it. This involves high costs in terms of money and maintenance and calibration time.

It is therefore a desirable object in itself to reduce the number of test units. But if there is to be no reduction in the bottle throughput, it is necessary for the measuring time per bottle to be shortened, because with a reduced number of test units each unit will have to test more than one bottle in a given period of time. It to must particularly be borne in mind, however, that not only is the actual measuring time for the individual gas sample in the test apparatus significant, but also allowance must be made for a recovery time which the test apparatus requires after heavy contamination has been detected in order to regain sufficient sensitivity to detect a low level of contamination; this phenomenon is sometimes called the "memory effect". Such an effect occurs in all suitable types of testing apparatus for the gas samples, including the PID test apparatus already mentioned, and including mass spectrometers.

SUMMARY OF THE INVENTION

It is therefore the basic task of the invention to provide a testing process for bottles which, despite a high bottle throughput allows testing to be performed with a small number of test units and/or with which the memory effect of the test apparatus does not reduce the bottle throughput so that bottle testing can proceed with relatively low equipment cost in terms of money and maintenance and calibration time.

This is accomplished in a process of the type stated at the outset by testing each bottle by means of at least two testing stations arranged in succession along the conveyor path, the first testing station having a contamination response threshold which is a multiple of the contamination detection threshold of the second testing station, and by deactivating the second testing station when bottles whose contamination has produced a response at the first testing station pass through the second testing station.

According to an alternative configuration of the process, bottles whose contamination has produced a response at the first testing station are removed from the conveyor path before reaching the second testing station.

The first testing station—which checks for contamination with a relatively high response threshold—is capable of detecting heavily contaminated bottles. These bottles then pass through the second testing station, but are not tested in the second, more sensitive, testing station. Alternatively, they are removed before reaching it. The second testing station is thus relieved of testing heavily contaminated bottles which would evoke a pronounced memory effect. This means that, on the one hand, the second testing station can have a low detection threshold for contamination (which is desirable in order that harmful contaminants can be detected even if present in low concentrations), yet no time-critical memory effect can occur since the heavily contaminated bottles which would cause this are either not being tested in the second testing station, or are not passing through it. The dynamic range which has to be covered by the second testing station is therefore trimmed at the top end, ie. at the heavy contamination end, by the first testing station, yielding the aforesaid positive effects at the second testing station. At the first testing station, the memory effect is not critical, as only heavy contamination needs to be detected there, which is possible after a very short recovery time even if the preceding contamination has been heavy. Here, therefore, tee dynamic range is trimmed at the bottom end, is at the low contamination end, with the first station only responding to heavy levels of contamination. It would be perfectly possible in principle to use a first testing station which also has a low detection threshold, but with the response level at which the testing station is activated set relatively high.

This matching of the ranges of the two testing stations makes it possible, in a preferred way of carrying out the process according to the invention, for the second and advantageously very sensitive test to take the form of a mass spectrometric analysis whose pronounced and normally disadvantageous memory effect is largely curtailed by both alternative forms of the process according to the invention, so that the mass spectrometer is able to carry out bottle readings in rapid succession and a high bottle throughput can be sustained. As a low-cost method of performing the first test, photo-ionization detection is used. Preferably, for the contaminated bottles which are not tested, the gas sampling head is not inserted into the bottle. This is to prevent contamination of the head. In a further preferred way of carrying out the process, a shutter element is actually deployed over the bottle mouth in order reliably to prevent gas from being picked up from the dirty bottle.

It is also the basic task of the invention to provide an apparatus for carrying out the process.

BRIEF DESCRIPTION OF THE DRAWINGS

Examples of embodiments of the invention will now be described in detail with reference to the drawings, in which:

FIG. 1 shows diagrammatically a conveyor system for bottles with two testing stations;

FIG. 3 is a flow chart of the various tests on each bottle;

DESCRIPTION OF THE PREFERRED EMBODIMENTS

Figure 2:
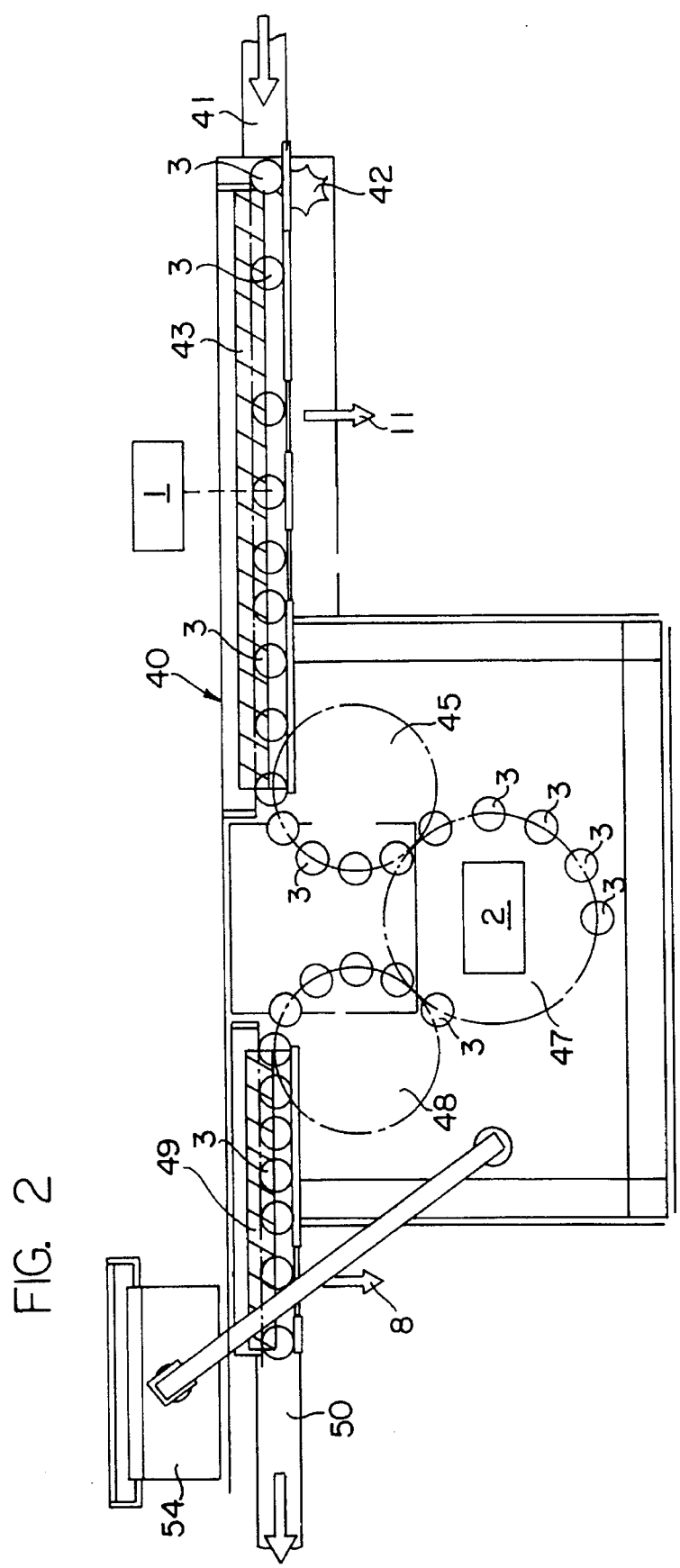
FIG. 2 is a diagrammatic plan view of a special configuration of the conveyor system.

FIG. 1 shows diagrammatically a belt conveyor 6 on which bottles are conveyed in an upright position. The bottles in this example are returnable PET bottles which after the test now to be described am fed to a washing machine and then refilled with a drink product. The testing apparatus according to the invention uses two testing stations Testing station 1 detects heavy contamination of the bottle with harmful substances, including such substances is petrol, solvents, paints, insecticides, alcohol, etc. A gas sample is taken from each bottle by the testing station 1. This sampling can be performed e.g. by means of a probe 4 which can be lowered into the bottle, as shown in the diagram. However, especially in the case of station 1 for heavy contamination, it may suffice to draw gas from above the bottle mouth. Air can also be blown into the bottle to facilitate withdrawal of a gas sample. The gas sample which has been withdrawn is analyzed, preferably by photo-ionization detection, in a known manner. An example of a suitable apparatus is the Model PI 52-02A Photo-Ionization Detector made by HNU Systems, Inc. The response threshold is set so that heavily contaminated bottles are reliably detected. Information as to the presence of a bottle thus contaminated is output to a control unit 9. According to the signal from testing station 1, the control unit controls testing station 2 so that bottles identified as dirty are not tested by testing station 2. Alternatively, the control unit 9 controls a rejector device 7 (depicted in broken lines) which is located downstream of the testing station 1 in the conveying direction, and which rejects from the conveyor system the bottle identified as contaminated, or ejects it onto another conveyor belt before it reaches the testing station 2.

Bottles passed as clean by station 1 are retested by testing station 2 for the presence of harmful substances. By now, however, there is no need to deal with very high concentrations of harmful substances in the gas sample, which means that a low detection threshold can be chosen without requiring an extended decay time for the memory effect between readings. Thus, even with high sensitivity, readings can be taken in rapid succession, allowing a high bottle throughput. Here again, readings are obtained by taking a gas sample from the bottle by means of an insertable probe 5. At this point the analysis is preferably performed with a standard commercial mass spectrometer, which affords a particularly accurate analysis even at low levels of contamination, and hence an unambiguous decision as to whether or not the bottle is still usable. Depending On the outcome of the analysis, unusable bottles are ejected from the conveyor path, or diverted onto another conveyor belt, by a further rejector 8. Instead of the mass spectrometer, however, the testing station 2 can be equipped with the photo-ionization detector which has already been mentioned.

FIG. 2 shows diagrammatically a plan view of a bottle testing apparatus 40 operating in accordance with the process. Returned bottles are randomly fed to the device on a conveyor line 41. The bottles are fed to the apparatus in the upright position and are normally open, ie. uncapped, and are not yet washed. By means of a conveyor and the resulting backup pressure, bottles 3 are supplied to a rotary star 42, which also forms the line stop, and are released into a worm conveyor 43 which feeds the bottles at regular intervals and in an upright position. A number of testing devices can be provided along this conveyor section upstream of the testing station 1, and these will be described in detail with reference to FIG. 3. In particular, the bottles can be checked for correct height, and for the presence of a cap of other stopper and of residual liquid. Unsuitable bottles can be rejected from the worm conveyor by an ejector 11. The bottles then pass through the testing station 1, which comprises a photo-ionization detector, and if detected as dirty are identified accordingly in the control device, or in the alternative procedure are removed from the conveyor path by another ejector (not shown). The bottles 3 having undergone this preliminary test pass from the worm conveyor 43 onto a feed carousel 45. From this feed carousel 45 the bottles are fed to a main carousel 47. Testing in test station 2, e.g. in the form of a mass spectrometric analysis, is performed while the bottles are in the main carousel 47. Only four bottles 3 are shown diagrammatically in FIG. 2. In reality the main carousel is capable of receiving a larger number of bottles to be tested, e.g. 16 bottles, which are tested by a mass spectrometer located above the main carousel. After testing, the bottles pass via a discharge carousel 48 to a discharge worm conveyor 49. A further ejector 8 is located at this discharge worm conveyor to reject those bottles which have been identified by the mass spectrometer as contaminated.

Rejection may be performed in various known ways, e.g. by means of a jet of compressed air, or by an electromechanically operated pushrod-type ejector. However, the preferred method is to use a "soft" diversion system whereby those bottles which are to be removed are guided in an upright position on to another conveyor line in this way, overturning of bottles containing possibly harmful liquids can be avoided. These bottles are conveyed, in an upright position, to a disposal point. Downstream of the worm conveyor 49, the uncontaminated bottles are discharged to a conveyor line 50 which conveys them to a washing station and then onwards to a filling station. A control box 54 is arranged on a boom. The controls for the apparatus as a whole can be separately accommodated.

FIG. 3 shows diagrammatically the steps in the testing process in the apparatus according to FIG. 3. The incoming bottles on the conveyor line arrive at the star wheel 42, where non-upright bottles cause a line stop. In the feed worm-conveyor, the height of each individual bottle is then checked by means of two photoelectric barriers. Oversize or undersize bottles are eliminated. The next check is performed by means of an ultrasonic sensor which detects whether the cap has been removed from each bottle. Bottles with caps or other stoppers are eliminated. A weight sensor is then used check whether a relatively large quantity of residual liquid is present in the bottle. If so, the bottle is eliminated.

Those bottles which have not been eliminated pass on, as already described, to the testing station 1.

Figure 4:
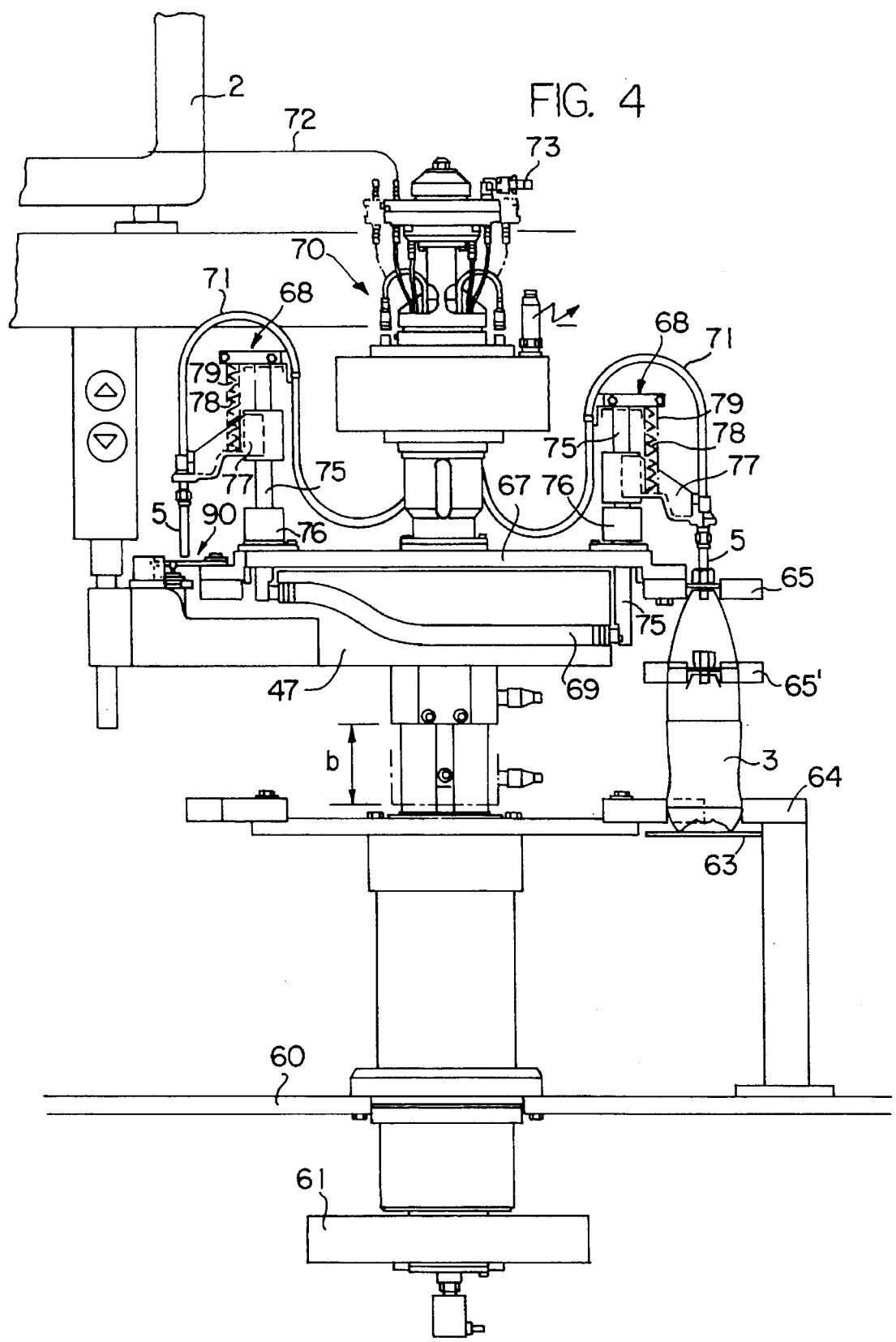
FIG. 4 is an elevation of the main carousel of FIG. 2.

FIG. 4 shows the main carousel 47 of FIG. 2, two bottle holders and only one bottle 3 are shown. The carousel is arranged on a fixed supporting table 60 and is rotated by a drive wheel 61 of a motor not shown in the drawing. The bottles 3 move over a bottom guide plate 63 which is fired to the machine. They are held at their lower end in a surrounding outer guide 64 which extends around the central axis of the carousel, and are held at the bottle neck in a surrounding outer guide 65. The distance between the guides 64 and 65 can be adjusted by shifting the upper part of the carousel with respect the lower part of the carousel, as shown by the arrow b and by the guide-outline 65' indicating the guide 65 in its lower position for shorter bottles. Mounted at each bottle position on the revolving upper carousel table 67, in addition to the said outer guides 65, is a double-acting lifting unit 68 which carries the gas sampling tube 5 for each bottle. Thus, a carousel with 16 bottle positions is fitted with 16 such double-acting lifting units 68 Their function will be explained presently. Each double-acting lifting unit 68 carries a gas sampling tube 5 connected to a central valve head 70 by a hose 71. In the central valve head, the air extracted from the bottles 3 is directed to a single conduit 72 which leads to the mass spectrometer 2 which is merely outlined in the drawing. Preferably during the greater part of the circuit of each bottle 3 in the carousel, gas is extracted from the bottle 3 by means of a central vacuum pump (not shown) which is connected to the connection 73 on the valve head 70. Within the valve head 70, connection is briefly established at any given time between one of the gas sampling tubes 5 and the mass spectrometer 2, while the other gas samples are conveyed to the pump via the connection 73. In this way, the effect on the measuring time of the extended path from the sampling tube 5 to the valve head 70 is eliminated.

In the apparatus shown in FIG. 4, a shutter is provided over each bottle 3 which is able to prevent the gas sampling tube 5 from dipping into the bottle 3. In FIG. 4 this shutter 90 is Only depicted under the sampling tube 5 on the left-hand side of the drawing and has been omitted at the right-hand sampling tube although such a shutter is fitted at that location also. The construction of the shutter will be explained in detail with reference to FIG. 5. Each double-acting lifting unit 68 has a tappet 75 which is slidably held in a guide 76. The bottom end of each tappet engages a cam 69 which is fixed against the carousel part 47. As t-he carousel part 67 revolves, the cam 69 causes a vertical displacement of the tappet 75. The tappet 75 shown on the right-hand side of FIG. 4 is in its lower end position, with the gas sampling tube 5 dipping into the bottle 3; and the tappet 75 shown on the left-hand side of FIG. 4 is in its upper end position, in which the gas sampling tube 5 is no longer inserted in the bottle, and is positioned above the shutter 90. The gas sampling tubes 5 are mounted on a carriage 77 which is able to slide along the tappet. Normally, however, the carriage 77 is urged by a spring 78 into an end position of its travel on the tappet 75 the gas sampling tube 5 is able to dip into the bottle without encountering resistance, there is no relative movement between the carriage 77 and the tappet 75, and the carriage 77 follows the movement of the tappet 75 imparted by the cam 69 and dips into the bottle or withdraws from the bottle as the case may be. When, however, the shutter 90 is closed, as will be illustrated presently, the gas sampling tube 5 hits the shutter 90 when the tappet 75 drops, and therefore cannot be lowered into the bottle 3. In this case, although the tappet 75 continues moving downwards to perform its lowering movement, the gas sampling tube 5 and carriage 77 do not perform this downward movement. There is a displacement of the tappet 75 relative to the stationary carriage 77, so that the spring 78 is tensioned. During the circuit of this bottle which has been barred by the shutter 90 the gas sampling tube 5 remains blocked above the bottle and when in this position draws no air out of the bottle 3, as the shutter 90 prevents this. When the tappet 75 is raised, it first of all rises relative to the carriage 77, which remains stationary, until the normal position of the carriage 77 on the tappet 75, which is defined by the stop bar 79 surrounded by the spring 78, is reached. Once the normal position of tappet and carriage with respect to one another has been restored by the spring 78 when the tappet 5 is raised, these elements resume their synchronized motion (unless the gas sampling tube 5 is prevented by the shutter 90 from dipping into the next bottle presented).

Figure 5:
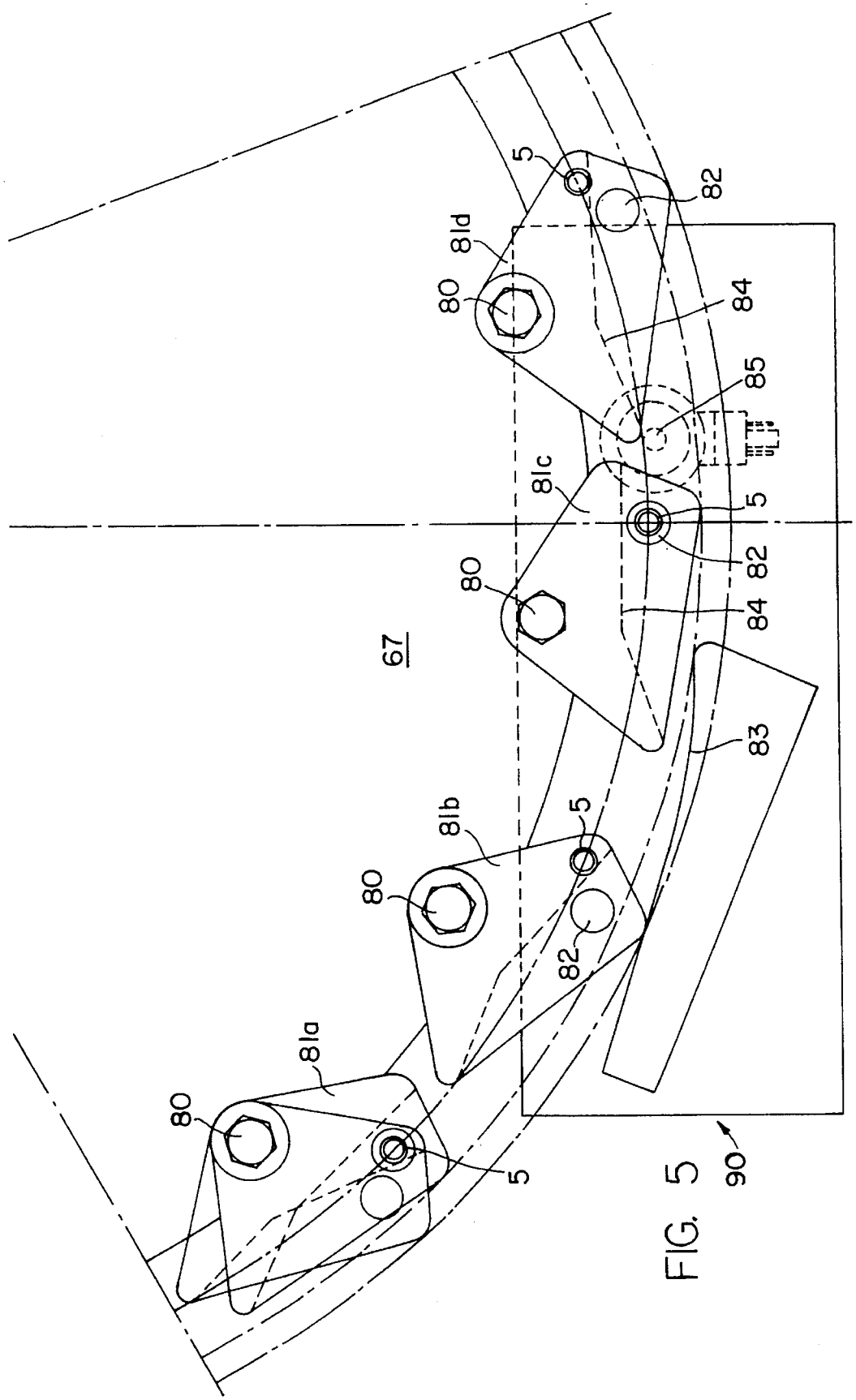
FIG. 5 is a partial view of the shutter mechanism.

FIG. 5 shows part of the shutter 90. The carousel part 67, rotating in the direction of the arrow, is seen from above. At every bottle position this part is fitted with a shutter leaf 81, rotatable about a pivot 80. Thus if there are 16 bottle positions, 16 of these leaves 81 are fitted. The leaves 81 have an opening 82 to allow the gas sampling tube 5 to pass through. Depending on the pivoting position of the individual leaf 81 (open-port position or closed position), the tube 5 positioned above the leaf 81 is either able to or unable to enter the bottle 3 when lowered. To set the leaves 84, these are first reset in the open position in each revolution by a cam 83, as can be seen in the case of leaf 81c. Leaves 81 are then individually set in the closed position by an electromagnetically operated pushrod 85 actuated by the control unit, which is able to engage a control face 84 on the underside of each leaf 81, as shown for leaf 81d, when this is necessitated by The result of the test at testing station 1 for the bottle 3 assigned to the leaf concerned, that is to say when the bottle in question has been identified as dirty. The closure of the leaf, as shown for leaf 81d, prevents the sampling tube 5 from being lowered into the bottle throughout the circuit of the bottle on the carousel. After this dirty bottle has left the carousel, the leaf again arrives at the resetting cam 83, where it is moved to the open position and then remains in that position provided the next bottle is a clean one; or the leaf is closed again if the next bottle 3 assigned to the leaf is another dirty one.

Instead of the illustrated forced actuation of the sampling tubes 5 by the motion of the carousel, each tube 5 can be provided with an individually controllable drive. In this case, the shutter mechanism 90 can be dispensed with.

The gas sampling tube 5 is then individually controlled by the control unit and is or is not inserted into the bottle 3 by its individual drive unit according to whether the bottle coming on to the carousel is to be tested, or is a dirty bottle which is not to be tested. However, the illustrated scheme with the shutter mechanism 90 affords the particular advantage that the individual leaf 81 forms a barrier to the withdrawal of gas from the bottle 3, whereas such withdrawal is still possible, albeit in small amounts, when no such barrier is present, even when the tube 5 is in the non-inserted position above the bottle 5.

We claim:

1. Apparatus for testing returnable bottles for refilling, comprising:

a conveyor system for returning bottles;

a first testing station arranged on the conveyor system including a gas sampling unit and a photoionization detector for testing gas samples taken from bottles returned for refilling at a predetermined detection threshold indicative of a predetermined high level of contamination;

a second testing station arranged in the conveyor system downstream of the first testing station in the bottle conveying direction including a further gas sampling unit and a testing unit for testing further gas samples taken from bottles at a detection threshold indicative of a level of contamination lower than the predetermined level; and means arranged between the gas sampling units for selectively removing bottles from or permitting bottles to proceed along the conveyor path based upon test results of the gas samples taken at the first testing station, so that bottles in which the contamination exceeds the predetermined level are removed from the conveyor system prior to being tested at the second testing station, and bottles which do not exceed the predetermined level are tested a second time.

2. Apparatus according to claim 1, characterized in that the testing unit comprises a photo-ionization detector.

3. Apparatus according to claim 1, characterized in that the testing unit comprises a mass spectromer.

4. Apparatus for testing returnable bottles sent back for refilling comprised by:

a conveyor system for the bottles, a first testing station arranged on the conveyor system for testing bottles for a predetermined level of contamination, which station includes a first gas sampling unit and a first testing unit producing an output signal indicative of the test results, a second testing station arranged on the conveyor system downstream of the first testing station in the bottle conveying direction with a second gas sampling unit and a second testing unit for testing the bottles for a level of contamination less than the predetermined level, and control means for selectively preventing the testing of bottles at the second testing station in accordance with the output signal from the first testing unit, the control means including means for removing a bottle which has a contamination level greater than the predetermined level from the conveyor system between the first and second testing stations or for permitting the bottle to proceed along the conveyor system, so that bottles which exceed the predetermined contamination level are removed from the conveyor system prior to being tested at the second testing station, and only bottles which do not exceed the predetermined contamination level are tested a second time for a contamination level less than the predetermined level.

\* \* \* \* \*